United States Patent
Marshall et al.

(10) Patent No.: US 9,901,731 B2
(45) Date of Patent: Feb. 27, 2018

(54) MEDICAL ELECTRICAL LEAD HAVING IMPROVED INDUCTANCE

(75) Inventors: Mark T. Marshall, Forest Lake, MN (US); Kevin R. Seifert, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 2345 days.

(21) Appl. No.: 11/343,655

(22) Filed: Jan. 31, 2006

(65) Prior Publication Data
US 2007/0179577 A1    Aug. 2, 2007

(51) Int. Cl.
*A61N 1/05* (2006.01)
*A61N 1/37* (2006.01)
*A61N 1/08* (2006.01)

(52) U.S. Cl.
CPC ............. *A61N 1/056* (2013.01); *A61N 1/08* (2013.01); *A61N 1/3718* (2013.01)

(58) Field of Classification Search
CPC ......... A61N 1/3718; A61N 1/08; A61N 1/056
USPC .................................. 607/112, 116
See application file for complete search history.

(56) References Cited

U.S. PATENT DOCUMENTS

| | | |
|---|---|---|
| 4,135,518 A | 1/1979 | Dutcher |
| 4,493,329 A | 1/1985 | Crawford et al. |
| 4,643,202 A | 2/1987 | Roche |
| 5,056,516 A | 10/1991 | Spehr |
| 5,231,996 A | 8/1993 | Bardy et al. |
| 5,276,398 A * | 1/1994 | Withers et al. ............... 324/318 |
| 5,330,522 A | 7/1994 | Kreyenhagen |
| 5,387,199 A | 2/1995 | Siman et al. |
| 5,425,755 A | 6/1995 | Doan |
| 5,456,707 A | 10/1995 | Giele |
| 5,522,875 A | 6/1996 | Gates et al. |
| 5,584,873 A | 12/1996 | Shoberg et al. |
| 5,599,576 A | 2/1997 | Opolski |
| 5,935,159 A | 8/1999 | Cross, Jr. et al. |
| 5,957,970 A | 9/1999 | Shoberg et al. |
| 5,968,087 A | 10/1999 | Hess et al. |
| 6,078,840 A | 6/2000 | Stokes |
| 6,178,355 B1 | 1/2001 | Williams et al. |
| 6,249,708 B1 | 6/2001 | Nelson et al. |
| 6,289,250 B1 | 9/2001 | Tsuboi et al. |
| 6,295,476 B1 | 9/2001 | Schaenzer |
| 6,400,992 B1 | 6/2002 | Borgersen et al. |
| 6,434,430 B2 | 8/2002 | Borgersen et al. |
| 6,493,591 B1 | 12/2002 | Stokes |
| 6,501,991 B1 | 12/2002 | Honeck et al. |

(Continued)

FOREIGN PATENT DOCUMENTS

| | | |
|---|---|---|
| FR | 2 494 118 | 5/1982 |
| WO | WO030063946 A2 | 8/2003 |
| WO | WO20050030322 A | 4/2005 |

OTHER PUBLICATIONS

International Search Report, PCT/US2007/060677, dated Apr. 18, 2007, 5 Pages.

*Primary Examiner* — Michael D Abreu

(57) ABSTRACT

A conductor for connecting an electrode near a distal end of a medical electrical lead with an implantable medical device connected with a proximal end of the medical electrical lead includes a multi-filar coil wrapped around a central core. The multi-filar coil has an inductance of approximately 0.5 µH or greater, and the central core is non-conducting and provides reinforcement for the multi-filar coil.

18 Claims, 4 Drawing Sheets

(56) References Cited

U.S. PATENT DOCUMENTS

| | | | |
|---|---|---|---|
| 6,501,994 B1 | 12/2002 | Janke et al. | |
| 6,516,230 B2 * | 2/2003 | Williams et al. | 607/116 |
| 6,813,521 B2 | 11/2004 | Bischoff et al. | |
| 6,854,994 B2 | 2/2005 | Stein et al. | |
| 6,925,334 B1 | 8/2005 | Salys | |
| 7,013,180 B2 | 3/2006 | Villaseca et al. | |
| 7,289,846 B2 | 10/2007 | Shoberg et al. | |
| 7,844,343 B2 | 11/2010 | Wahlstrand et al. | |
| 2003/0083726 A1 | 5/2003 | Zeijlemaker et al. | |
| 2003/0144716 A1 | 7/2003 | Reinke et al. | |
| 2003/0144718 A1 | 7/2003 | Zeijlemaker | |
| 2003/0144719 A1 | 7/2003 | Zeijlemaker | |
| 2003/0144720 A1 | 7/2003 | Villaseca et al. | |
| 2003/0144721 A1 | 7/2003 | Villaseca et al. | |
| 2004/0193140 A1 | 9/2004 | Griffin et al. | |
| 2005/0027342 A1 | 2/2005 | Shoberg et al. | |
| 2005/0055068 A1 | 3/2005 | Von Arx et al. | |
| 2005/0197677 A1 * | 9/2005 | Stevenson | 607/36 |
| 2005/0222656 A1 | 10/2005 | Wahlstrand et al. | |
| 2005/0222657 A1 * | 10/2005 | Wahlstrand et al. | 607/116 |
| 2005/0222658 A1 | 10/2005 | Hoegh et al. | |
| 2005/0222659 A1 | 10/2005 | Olsen et al. | |
| 2005/0246007 A1 | 11/2005 | Sommer et al. | |
| 2006/0041294 A1 | 2/2006 | Gray | |
| 2006/0229693 A1 | 10/2006 | Bauer et al. | |
| 2006/0252314 A1 * | 11/2006 | Atalar et al. | 439/876 |

* cited by examiner

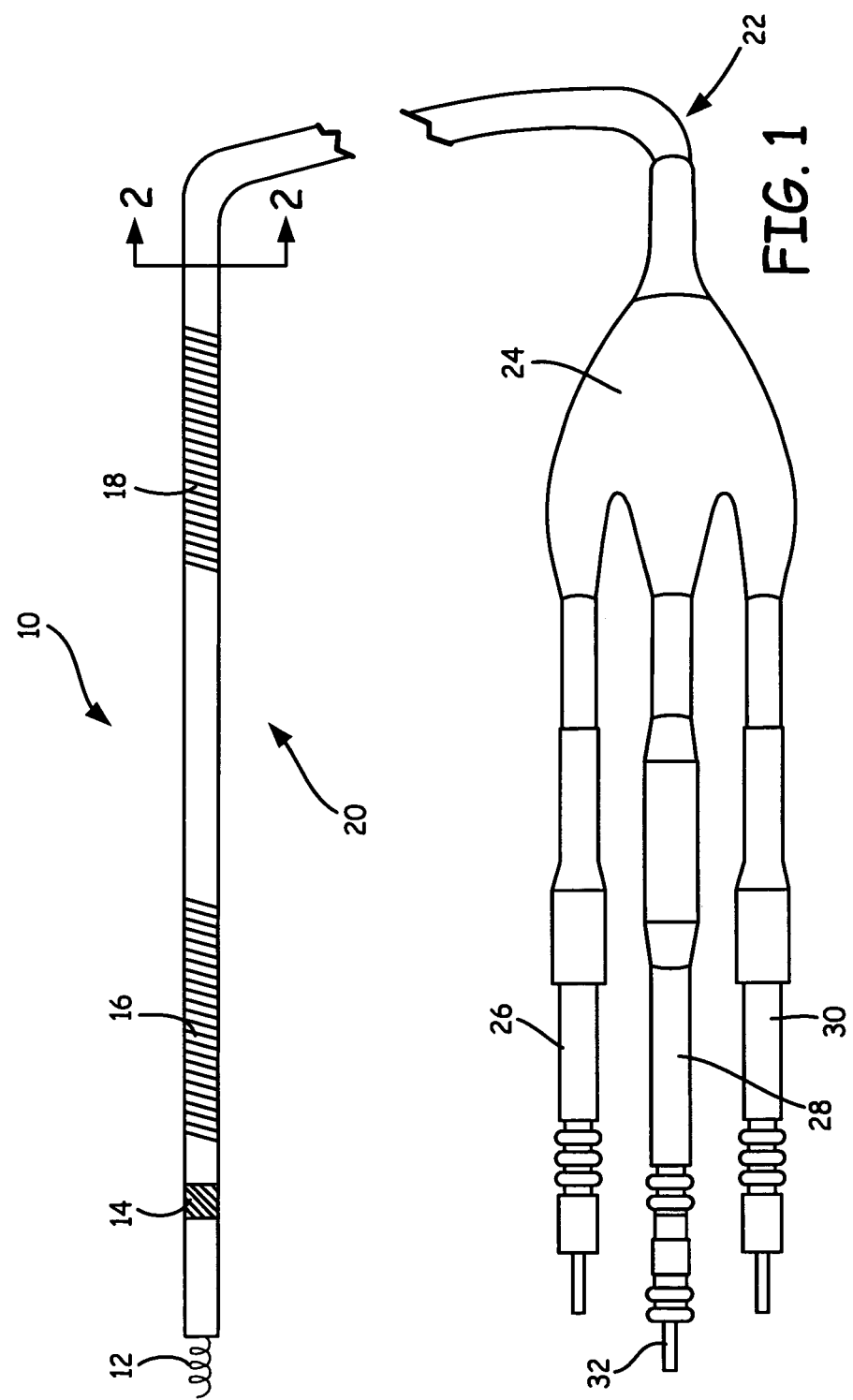

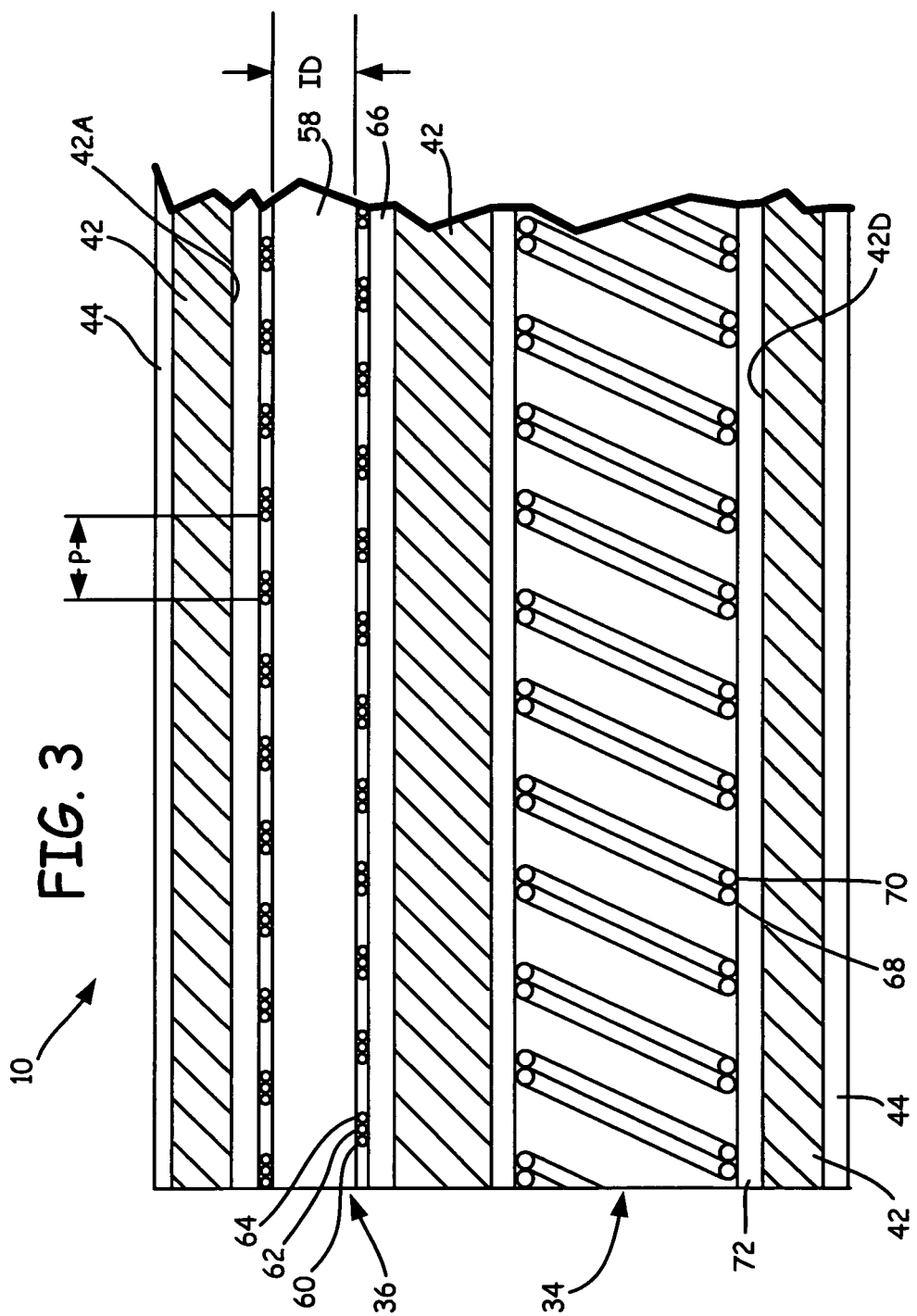

MEDICAL ELECTRICAL LEAD HAVING IMPROVED INDUCTANCE

CROSS REFERENCE TO RELATED APPLICATION(S)

The following co-pending application is filed on the same day as this application: "POLYMER REINFORCED COIL CONDUCTOR FOR TORQUE TRANSMISSION" by inventors M. T. Marshall and H. D. Schroder, U.S. application Ser. No. 11/343,884, now abandoned and is incorporated herein by reference.

BACKGROUND OF THE INVENTION

The present invention relates generally to implantable medical device (IMD) leads for delivering active electrodes to various places in a human body, such as the heart. In particular, the present invention relates to lead conductors that are compatible with radio frequency (RF) fields generated by magnetic resonance imaging (MRI).

Typical leads for use with an IMD, such as an implantable cardioverter defibrillation (ICD) device, deliver multiple conductors to the heart for performing pacing, cardioverting, defibrillating, sensing and monitoring functions. One or more of these conductors typically comprises a multi-filar cable in which nineteen filars are wrapped around a straight central filar. This type of design yields a cable that has good mechanical properties, including flexibility, weldability and high strength. Strength is particularly important for ensuring adequate electrical and mechanical contact between the conductor and an electrode when an electrode is crimped down on the conductor. For example, a good crimp should produce a 2.5 lbf joint. These multi-filar, cables, however, have very low inductance particularly due to the straight central filar. During magnetic resonance imaging, it is necessary to expose the patient and the IMD to a radio-frequency field, which is used to generate the MRI image. Generally, it is desirable for a lead conductor to have increased inductance in order to minimize excitation effects from RF fields generated during magnetic resonance imaging.

BRIEF SUMMARY OF THE INVENTION

The present invention comprises a strength-enhanced conductor for a medical electrical lead. The conductor connects an electrode near a distal end of a medical electrical lead with an implantable medical device connected to a proximal end of the medical electrical lead, and includes a multi-filar coil wrapped around a non-conducting central core. The multi-filar coil includes an inductance of approximately 0.5 µH or greater.

BRIEF DESCRIPTION OF THE DRAWINGS

FIG. 1 shows a medical electrical lead of the present invention for use with an implantable cardioverter defibrillation (ICD) device.

FIG. 3 shows cross section 3-3 of FIG. 2A.

DETAILED DESCRIPTION

Figure 2A:
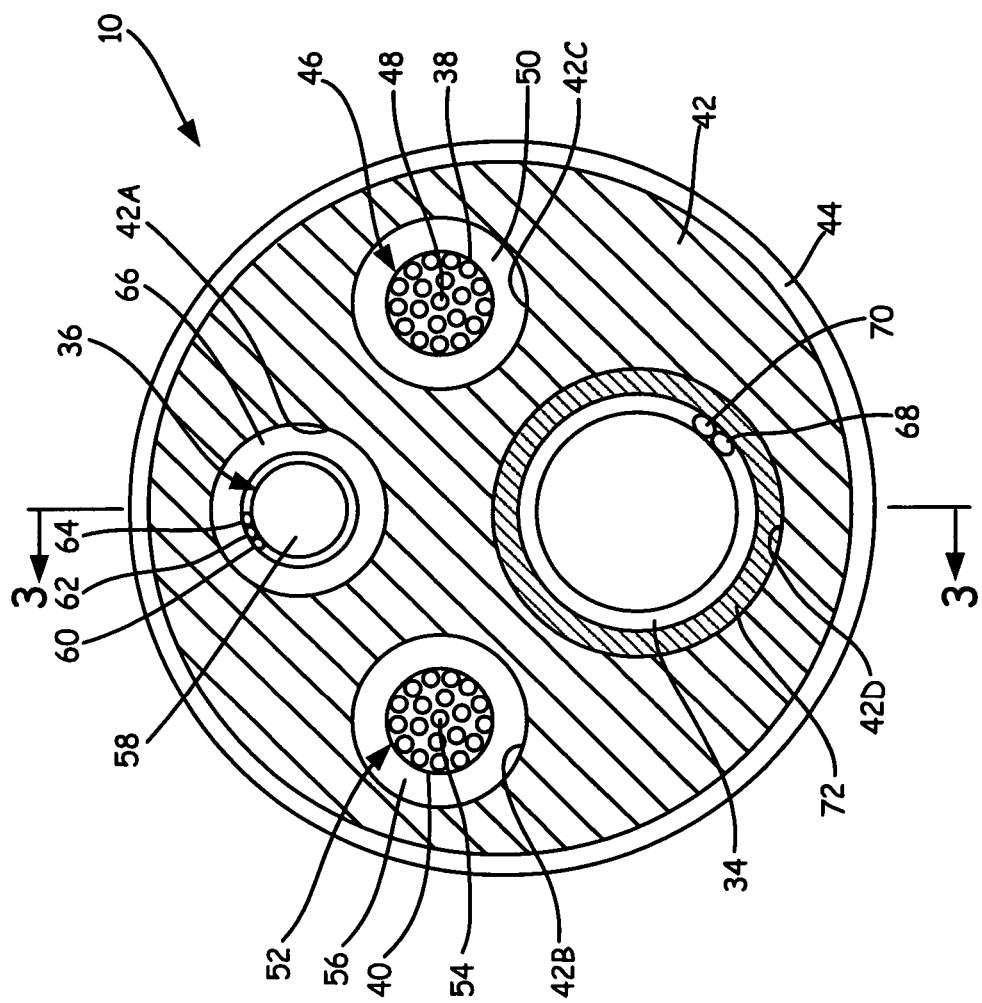
FIG. 2A shows cross section 2-2 of FIG. 1 showing the conductors of the ICD lead.

FIG. 1 shows implantable cardioverter defibrillation (ICD) lead 10 of the present invention. ICD lead 10 is used to deliver tip electrode 12, ring electrode 14, right ventricle (RV) defibrillation coil 16 and superior vena cava (SVC) defibrillation coil 18 to a heart for the purposes of providing cardio-therapy.

Tip electrode 12, ring electrode 14, RV coil 16 and SVC coil 18 are connected at distal end 20 of ICD lead 10 with various conductors that run to proximal end 22 of ICD lead 10, where the conductors are joined with connector assembly 24. Connector assembly 24 routes the individual conductors to connectors 26, 28 and 30 for connection with connector sockets of an implantable medical device (IMD).

Tip electrode 12 and ring electrode 14 are connected with connector 28 and with a conductor coil and a conductor cable, respectively, which are electrically isolated within lead 10. Tip electrode 12 and ring electrode 14 are used to sense cardiac signals and to deliver pacing pulses to the right ventricle of the heart in conjunction with the IMD. RV coil 16 is joined with connector 26, and SVC coil 18 is joined with connector 30 through conductor cables, which are electrically isolated from each other within in lead 10. RV coil 16 (which is placed in the right ventricle) and SVC coil 18 (which is placed in the superior vena cava) can be used as cathode and anode to deliver defibrillation shocks to the heart from the IMD, as a result of a tachycardia or fibrillation condition sensed in the heart by tip electrode 12 and ring electrode 14.

Tip electrode 12 typically comprises a fixation device, such as a helix or corkscrew, which is used to secure tip electrode 12 to tissue of the right ventricular apex of the heart. A fixation helix comprises a rigid coil with a sharpened tip that can penetrate into the tissue in order to anchor the position of tip electrode 12 within the heart. At the proximal end of lead 10, a rotational force is applied to a torque coil, which then transmits the torque to its distal end and the fixation helix, whereby it attaches to the heart tissue.

Figure 2B:
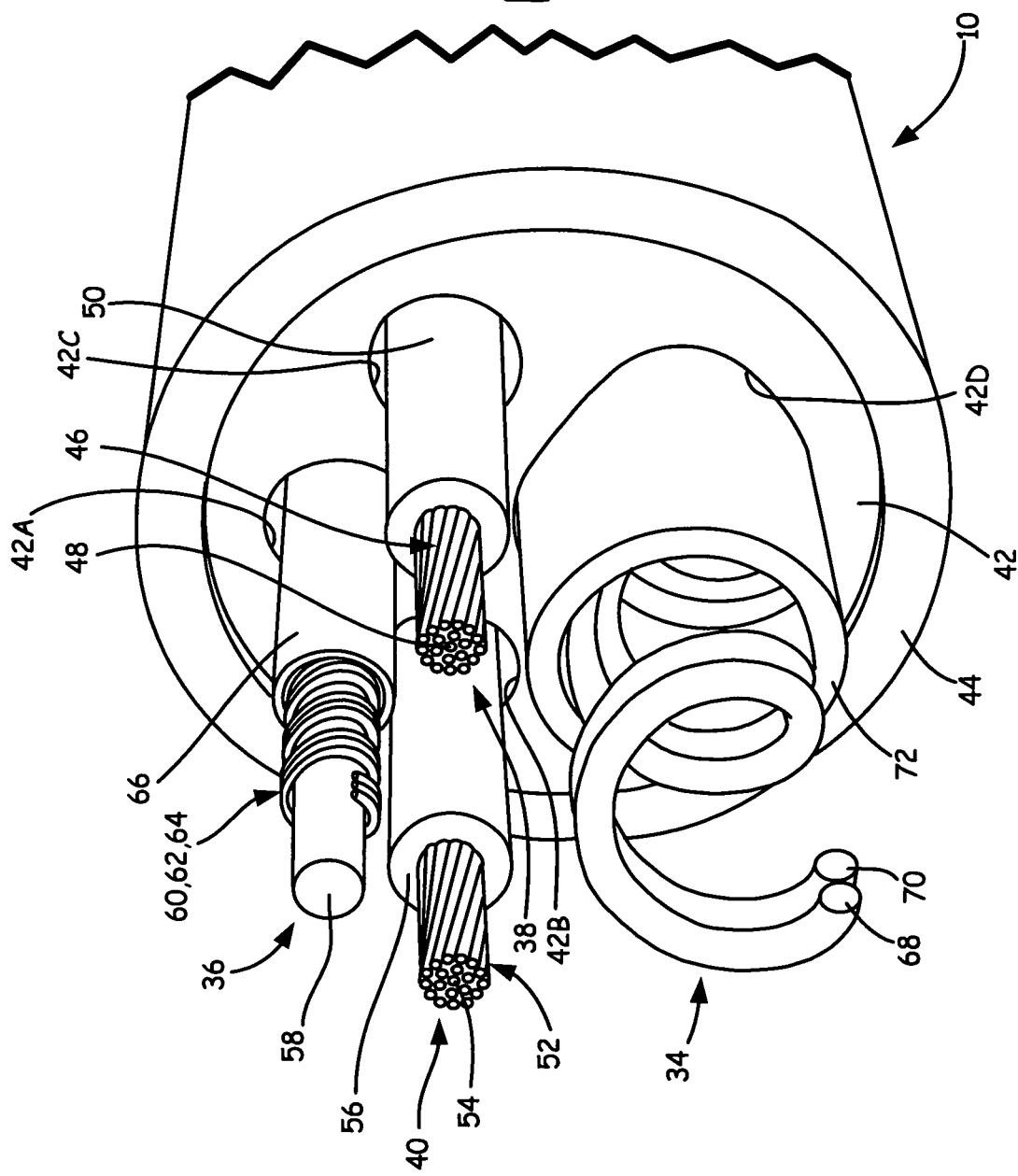
FIG. 2B shows a partially cut away perspective view of cross section 2-2 of FIG. 1.

FIG. 2A shows cross section 2-2 of FIG. 1 showing the conductors of lead 10, including coil conductor 34, sense conductor 36, RV conductor 38 and SVC conductor 40. FIG. 2B shows a partially cut away perspective view of cross section 2-2 of FIG. 1, in which the features of lead 10 are illustrated. FIGS. 2A and 2B are discussed concurrently.

ICD lead 10 includes multi-lumen lead body 42, which includes four lumens 42A-42D for conveying each of the four conductors of lead 10. Lead body 42 is typically comprised of extruded silicone rubber, and is covered by sheathing 44 that protects the components of lead 10 from the environment of the body in which it is implanted. Sheathing 44 is also comprised of extruded silicone rubber or another bio-compatible material.

As discussed above, exposure of IMD leads to MRI can result in localized heating of electrodes due to excitation of conductors from RF fields used in obtaining MRI images. When an electrode with a small surface area is vibrated by a conductor, excessive heat can build up in the electrode. High levels of vibration in an electrode are correlated with low inductance of the conductor to which it is connected. Conductors with high inductance are more resistant to excitation in RF fields, and are therefore more RF field compatible. For small electrodes, it is desirable to connect them with the IMD using conductors having a large inductance.

Generally, it is desirable for conductors used in conjunction with tip electrodes to have a total inductance in the range of about 1.0 µH to about 5.0 µH, preferably greater than about 1.5 µH. A large inductance is necessary due to the relative small surface area of tip electrodes, typically about 2.5 mm² (~0.003875 in²) to about 5 mm² (~0.00775 in²). For ring electrodes, which have surface areas in the range of about 20 mm² (~0.0310 in²), the inductance of the conductor can be as low as approximately 0.5 µH, but is preferably higher.

The inductance of a conductor is determined by its geometric properties, particularly if it is wound into a coil or straight. Straight wires have an inductance that approaches zero, and are therefore generally undesirable for small electrodes of leads that have the possibility of exposure to MRI. A conductor that includes straight filars in addition to wound filars also has an inductance that approaches zero.

The inductance of a wound coil is determined by several factors: the diameter of each wire conductor, the pitch of the coil (the distance between turns of the coil), the cross-sectional area occupied by the coil, and the number of filars comprising the coil. These parameters are constrained by the design requirements for each application in which the lead will be used. For example, a typical ICD lead must have an overall diameter less than approximately 6.6 French (~0.0866" or ~0.2198 cm).

RV conductor 38 comprises a stranded cable conductor in which nineteen wire filars 46 are wrapped around central wire filar 48 inside sheathing 50. Similarly, SVC conductor 40 comprises a stranded cable conductor in which nineteen wire filars 52 are wrapped around central wire filar 54 inside sheathing 56. The inductance of straight, central filars 48 and 52 effectively reduces the inductance of conductors 38 and 40 to zero. However, because RV conductor 38 and SVC conductor 40 are connected with RV coil 16 and SVC coil 18, which have large enough surface areas, excitation heating is not a concern and neither is the inductance of conductors 38 and 40.

Coil conductor 34 is connected with tip electrode 12, which has a relatively small surface area and is thus susceptible to excitation heating. Therefore, it is important for coil conductor 34 to have a high enough inductance to be RF field compatible. High inductance of coil conductor 34 must be achieved while also maintaining the torque transmitting capabilities of conductor coil 34. Therefore, the inductance of coil conductor 34 is increased, while maintaining the torque transmitting properties of the coil, utilizing an improved design, the details of which are described in the above referenced co-pending application by Marshall and Schroder. Coil conductor 34 is comprised of co-radially wound filars 68 and 70, that are enveloped in compression sheathing 72. In short, the inductance of coil conductor 34 is increased by reducing the number of filars in the coil. The pitch of coil conductor 34 can also be decreased to increase the inductance. In order to maintain the torque transmitting capabilities of coil conductor 34, compression sheathing 72 is extruded around coil conductor 34 in order to restrict radial expansion of the coil when it is placed under torque, thereby increasing its ability to transmit torque from its proximal to distal ends.

Turning to the present invention, conductor 36 is connected with ring electrode 14, which has a relatively small surface area for electrodes and is thus susceptible to excitation heating. Therefore, it is important for coil conductor 36 to have a high enough inductance to be RF field compatible. High inductance of conductor 36 must be achieved, however, while also maintaining a conductor that can produce crimps and welds of suitable strength. Conductor 36 comprises a multi-filar coil conductor, which is wrapped around a central non-conducting core to form a "coible." The inductance of sense conductor 36 is improved by replacing the low-inductance and conducting straight filar of previous designs with the non-conducting core. This eliminates the inductance of the straight wire filar, which essentially reduces the inductance of the entirety of conductor 36 to zero. Replacing the nineteen wire filars of previous designs is the multi-filar coil, which is wound around the core in a manner that increases the inductance of conductor 36.

FIG. 3 shows cross-section 3-3 of FIG. 2A, illustrating a longitudinal cross-section of lead 10 and the winding of conductor 36. Lead 10 includes coil conductor 34 and conductor 36, which are interposed in multi-lumen lead body 42 and wrapped in sheathing 44.

Coil conductor 34 includes conductor filars 68 and 70, which are wrapped in compression sheathing 72, which also acts as an insulator and as a protective barrier. Coil conductor 34 is connected with tip electrode 12 at its distal end and with connector 28 at its proximal end and is used to deliver pacing stimulus to the heart.

Conductor 36 includes conductor filars 60, 62 and 64, which are wound around core 58 and encased in sheathing 66. Filars 60, 62 and 64 are form a circuit with ring electrode 14 at their distal end and with connector 28 at their proximal end, and are used in conjunction with coil conductor 34 to perform typical sensing and pacing operations. In one embodiment, filars 60, 62 and 64 are uninsulated from each other and form a single circuit with ring electrode 14 and connector 28. In other embodiments, more or less filars are used for conductor 36. For example, in one embodiment, only two conductor filars are used to further increase the inductance for leads used with tip electrodes, where the electrode surface area is small.

Conductor 36 has an inner diameter ID, which approximately matches the outer diameter of core 58. Filars 60, 62 and 64 of conductor 36 are wound to have pitch p. The pitch p of coil conductor 36 is selected to produce a high enough inductance in coil conductor 36 to be RF field compatible, given the number of filars chosen for the particular design. In one embodiment, pitch p remains constant from near the proximal end to near the distal end of conductor 36. In the three-filar embodiment shown in FIG. 3, filars 60, 62 and 64 are comprised of 0.0018" (~0.0457 mm) diameter cobalt based sheath, silver core wire such as MP35N®, wound over a 0.007" (~0.1778 mm) diameter core and having a pitch of approximately 0.007" (~0.1778 mm). This configuration yields a conductor with an inductance of approximately 1.0 µH, which is suitable for use with ring electrodes having a surface area of about 20.0 mm² (~0.0310 in²). In other embodiments, similar wire materials can be used, such as Tantalum sheathings, or silver or gold cores.

In another three-filar embodiment, conductor 36 is comprised of 0.0012" (~0.0305 mm) diameter MP35N wire wound over a 0.005" (~0.127 mm) diameter core at a pitch of 0.006" (~0.1524 mm). This configuration also yields a conductor with an inductance of approximately 1.0 µH, which is also suitable for use with ring electrodes.

In another embodiment, a two-filar design includes 0.004" (~0.1016 mm) diameter MP35N® wire wound over an approximately 0.018" (~0.4572 mm) diameter core at a pitch of approximately 0.010" (~0.254 mm). This configuration yields a conductor with an inductance of approximately 2.5 µH, which is suitable for use with electrodes having small surface areas, such as tip electrodes with a 2.5 mm² (~0.003875 in²) or greater surface area.

In another embodiment, a four-filar design includes 0.001" (~0.0 mm) diameter filars wound over a 0.0055" core at a pitch of 0.006" (~0.0 mm). This yields a conductor with an inductance of approximately 0.5 mH, which is more suitable for use with electrodes having larger surface areas, such as ring electrodes.

Inner diameter ID approximately matches the outer diameter of non-conducting core 58 since filars 60, 62 and 64 are wrapped directly around core 58. In one embodiment, filars 60, 62 and 64 are wrapped tightly around core 58, but not so tight as to constrict or compress core 58 or to significantly reduce the flexibility of core 58. Core 58 is selected to be of a material having good mechanical properties and is non-conducting. Core 58 must be non-conducting so that it does not affect the inductance of conductor 36. Core 58 must have good strength so that ring electrode 14 can be properly crimped with conductors 60, 62 and 64, such that a sound electrical and mechanical connection is formed. Core 58 also provides tensile strength to conductor 36 when electrodes are connected with it. Also, core 58 must be able to withstand elevated temperatures produced during heat treatment of conductor 36. Core 58 must also have suitable flexibility for implantation and utilization of medical electrical lead 10.

Core 58 is comprised of a twisted multi-strand fiber, such as a liquid crystal polymer. In another embodiment, core 58 is comprised of expanded Teflon® (ePTFE). In other embodiments, core 58 is comprised of other materials that achieve the above mentioned properties and can have various constructions, such as solid, stranded or particle.

Conductor 36 is wrapped in sheathing 66, which is comprised of silicone rubber or another bio-compatible material, such as Ethylene Tetrafluoroethylene (ETFE). The thickness of the jacket is determined by the overall diameter of lead 10 and in one embodiment is 0.00115" (~0.0 mm) thick. Sheathing 66 serves as an insulating and protective barrier around conductor 36.

Although the present invention has been described with reference to preferred embodiments, workers skilled in the art will recognize that changes may be made in form and detail without departing from the spirit and scope of the invention.

What is claimed is:

1. A lead for an implantable medical device, the lead comprising:
    a lead body having a proximal end configured to couple to an implantable medical device and a distal end;
    multiple non-concentric lumens within the lead body;
    a first electrode located near the distal end of the lead body;
    a second electrode located near the distal end of the lead body and spaced from the first electrode;
    a first conductor for connecting the first electrode with the implantable medical device, the first conductor being positioned within a first lumen of the multiple lumens, the first conductor comprising:
        a central non-conducting core; and
        a multi-filar coil wrapped around the non-conducting core, the coil having a RF field compatible inductance, wherein filars of the multi-filar coil are uninsulated with respect to each other; and
    a second conductor for connecting the second electrode with the implantable medical device, the second conductor being positioned within a second lumen of the multiple lumens.

2. The lead of claim 1, further comprising:
    a third electrode positioned on the lead body proximally of the first and second electrodes; and
    a third conductor within a third lumen of the multiple lumens for connecting the third electrode with the implantable medical device.

3. The lead of claim 2, further comprising:
    a fourth electrode positioned on the lead body proximally of the first and second electrodes and spaced from the third electrode; and
    a fourth conductor within a fourth lumen of the multiple lumens for connecting the fourth electrode with the implantable medical device.

4. The lead of claim 3, wherein the first electrode is a ring electrode, the second electrode is a helical tip electrode, the third electrode is a coil electrode, and the fourth electrode is a coil electrode.

5. The lead of claim 1, wherein the the second conductor has an RF field compatible inductance of approximately 1.0 µH or greater.

6. The lead of claim 5, wherein the second electrode is a tip electrode that has a surface area of approximately 5 mm$^2$ or less.

7. The lead of claim 1, wherein the first electrode comprises a ring electrode and the first conductor has an RF field compatible inductance of approximately 0.5 pH or greater.

8. The lead of claim 7, wherein
    the second electrode is a tip electrode that is located at the distal end of the lead body; and
    the second conductor is a coil conductor for connecting the tip electrode with the implantable medical device, the coil conductor comprising one or more co-radially wound filars that have an RF field compatible inductance of approximately 1.0 pH or greater.

9. The lead of claim 1, wherein the second conductor is a coil with a larger coil diameter than the coil of the first conductor and wherein the second lumen has a larger diameter than a diameter of the first lumen.

10. A lead for an implantable medical device, the lead comprising:
    a lead body having a proximal end configured to couple to an implantable medical device and a distal end;
    a plurality of lumens within the lead body;
    a helical tip electrode located near the distal end of the lead body;
    a ring electrode located near the distal end of the lead body and spaced proximally from the helical tip electrode;
    a first conductor for connecting the ring electrode with the implantable medical device, the first conductor being located within a first lumen of the plurality of lumens, the first conductor comprising:
        a central non-conducting core; and
        a multi-filar coil wrapped around the non-conducting core, the coil having a RF field compatible inductance, wherein filars of the multi-filar coil are uninsulated with respect to each other; and
    a second conductor for connecting the helical tip electrode with the implantable medical device, the second conductor being located in a second lumen of the plurality of lumens, the second conductor comprising a multi-filar coil wrapped about open space of the second lumen.

11. The lead of claim 10, further comprising:
    a third electrode positioned on the lead body proximally of the first and second electrodes; and
    a third conductor for connecting the third electrode with the implantable medical device.

12. The lead of claim 11, further comprising:
    a fourth electrode positioned on the lead body proximally of the first and second electrodes and spaced from the third electrode; and a fourth conductor for connecting the fourth electrode with the implantable medical device.

13. The lead of claim 12, wherein the third electrode is a coil electrode and the fourth electrode is a coil electrode.

14. The lead of claim 12, wherein the third conductor is a stranded cable conductor and the fourth conductor is a stranded cable conductor.

15. The lead of claim 10, wherein the second conductor has an RF field compatible inductance of approximately 1.0 μH or greater.

16. The lead of claim 10, wherein the helical tip electrode has a surface area of approximately 5 mm² or less.

17. The lead of claim 10, wherein the first conductor has an RF field compatible inductance of approximately 0.5 μH or greater.

18. The lead of claim 10, wherein the second conductor is a coil with a larger coil diameter than the coil of the first conductor.

\* \* \* \* \*